(12) United States Patent
West et al.

(10) Patent No.: US 7,708,947 B2
(45) Date of Patent: *May 4, 2010

(54) METHODS OF MINIMIZING TEMPERATURE CROSS-SENSITIVITY IN VAPOR SENSORS AND COMPOSITIONS THEREFOR

(75) Inventors: Jeffrey A. West, Bellville, OH (US); Praveen Ramamurthy, Mansfield, OH (US)

(73) Assignee: Therm-O-Disc, Incorporated, Mansfield, OH (US)

( * ) Notice: Subject to any disclaimer, the term of this patent is extended or adjusted under 35 U.S.C. 154(b) by 1219 days.

This patent is subject to a terminal disclaimer.

(21) Appl. No.: 11/265,225

(22) Filed: Nov. 1, 2005

(65) Prior Publication Data

US 2007/0095678 A1    May 3, 2007

(51) Int. Cl.
*G01N 27/00* (2006.01)
(52) U.S. Cl. .................. 422/82.01; 422/82.02; 422/83; 422/96
(58) Field of Classification Search ............... 422/68.1, 422/82.01, 82.02, 83, 98, 84, 88, 90
See application file for complete search history.

(56) References Cited

U.S. PATENT DOCUMENTS

| | | | |
|---|---|---|---|
| 3,045,198 A | 7/1962 | Dolan et al. | |
| 3,234,180 A | 2/1966 | Wu | |
| 3,848,218 A | 11/1974 | Wakabayashi et al. | |
| 3,864,659 A | 2/1975 | Furuuchi et al. | |
| 4,129,030 A | 12/1978 | Dolan | |
| 4,224,595 A | 9/1980 | Dolan | |
| 4,592,967 A | 6/1986 | Komatsu et al. | |
| 4,621,249 A | 11/1986 | Uchikawa et al. | |
| 4,631,952 A | 12/1986 | Donaghey | |

(Continued)

FOREIGN PATENT DOCUMENTS

EP    0 434 396    6/1991

(Continued)

OTHER PUBLICATIONS

Grate, Jay, "Solubility Properties of Siloxane Polymers for Chemical Sensors", Proceedings of SPIE—The International Society for Optical Engineering, 2574 (1995), 71-7.

(Continued)

*Primary Examiner*—Sam P Siefke
*Assistant Examiner*—Dwayne K Handy
(74) *Attorney, Agent, or Firm*—Harness, Dickey & Pierce, P.L.C.

(57) ABSTRACT

The present invention relates to methods of making compositions for sensor films used for detecting chemical analytes within sensors, such as polymer-absorption chemiresistors (i.e., conductometric sensors). The sensor films have reduced cross-sensitivity to temperature, while maintaining sensitivity to the chemical analytes. The sensor matrix includes components that are associated with a first temperature coefficient of resistance, such as a polymer resin and/or a first conductive particle. The sensor matrix further comprises a second species, preferably a conductive particle, which has a second temperature coefficient of resistance that is opposite to the first temperature coefficient of resistance. The second species has an opposite influence on a resistance response of the sensor from the first species. In this manner, the sensor matrix exhibits a minimized response in resistance to any changes in temperature.

17 Claims, 3 Drawing Sheets

U.S. PATENT DOCUMENTS

| | | | |
|---|---|---|---|
| 4,673,910 A | 6/1987 | Uchikawa et al. | |
| 4,686,524 A | 8/1987 | White | |
| 4,691,186 A | 9/1987 | Shin et al. | |
| 4,752,761 A | 6/1988 | Dolan et al. | |
| 4,938,860 A | 7/1990 | Wogoman | |
| 5,150,603 A | 9/1992 | Boenning et al. | |
| 5,169,909 A | 12/1992 | Okawa | |
| 5,256,574 A | 10/1993 | Neuburger et al. | |
| 5,283,308 A | 2/1994 | Bilgrien et al. | |
| 5,571,401 A | 11/1996 | Lewis et al. | |
| 5,610,324 A | 3/1997 | Lawson | |
| 5,788,833 A | 8/1998 | Lewis et al. | |
| 5,837,164 A | 11/1998 | Zhao | |
| 5,862,030 A | 1/1999 | Watkins, Jr. et al. | |
| 5,891,398 A | 4/1999 | Lewis et al. | |
| 5,911,872 A | 6/1999 | Lewis et al. | |
| 5,951,846 A | 9/1999 | Lewis et al. | |
| 5,959,191 A | 9/1999 | Lewis et al. | |
| 5,979,227 A | 11/1999 | Lawson et al. | |
| 5,985,182 A | 11/1999 | Zhao | |
| 6,013,201 A | 1/2000 | Hayashida et al. | |
| 6,042,788 A | 3/2000 | De Wit et al. | |
| 6,074,576 A | 6/2000 | Zhao et al. | |
| 6,090,313 A | 7/2000 | Zhao | |
| 6,170,318 B1 | 1/2001 | Lewis | |
| 6,183,418 B1 | 2/2001 | Kuennecke | |
| 6,217,828 B1 | 4/2001 | Bretscher et al. | |
| 6,342,295 B1 | 1/2002 | Kobayashi | |
| 6,433,694 B1 | 8/2002 | Dolan et al. | |
| 6,444,323 B1 | 9/2002 | Matsumoto et al. | |
| 6,455,319 B1 | 9/2002 | Lewis et al. | |
| 6,518,371 B1 | 2/2003 | Fink et al. | |
| 6,815,520 B2 | 11/2004 | Yoneda et al. | |
| 6,868,350 B2 | 3/2005 | Zimmermann et al. | |
| 7,138,090 B2 * | 11/2006 | Blok | 422/82.01 |
| 7,171,312 B2 | 1/2007 | Steinthal et al. | |
| 7,501,091 B2 * | 3/2009 | Munoz et al. | 422/50 |

FOREIGN PATENT DOCUMENTS

| | | |
|---|---|---|
| EP | 0 833 421 | 4/1998 |
| EP | 1 088 849 | 4/2001 |
| EP | 1 215 248 | 6/2002 |
| EP | 1 254 924 | 11/2002 |
| EP | 1467199 | 10/2004 |
| EP | 1019715 | 1/2005 |
| JP | 02-309090 | 12/1990 |
| JP | 05-043823 | 2/1993 |
| JP | 07-258548 | 10/1995 |
| JP | 08-020725 | 1/1996 |
| JP | 08-120176 | 5/1996 |
| JP | 11-106657 | 4/1999 |
| JP | 2001-158856 | 6/2001 |
| JP | 2001-221225 | 8/2001 |
| SU | 1 582 597 | 11/1995 |
| WO | WO 96/37547 | 11/1996 |
| WO | WO 99/53300 | 10/1999 |
| WO | WO 01/50117 | 7/2001 |
| WO | WO 01/88042 | 11/2001 |
| WO | WO 02/08314 | 1/2002 |
| WO | WO 02/23134 | 3/2002 |
| WO | WO 02/086911 | 10/2002 |
| WO | WO 2004/107359 | 12/2004 |

OTHER PUBLICATIONS

Ho et al., "Review of Chemical Sensors for In-Situ Monitoring of Volatile Contaminants", SAND2001-0643 (Mar. 2001).

"Inco Special Products: Novamet and its Products: Nickel Oxides" [online], [retrieved on Sep. 21, 2005], retrieved from: www.incosp.com/novamet_products/nickel_oxides.

"Inco Special Products: Novamet Specialty Products" [online], [retrieved on Sep. 21, 2005], retrieved from: www.specon.com.au/Novamet.html.

Ronot et al., "Detection of Chemical Vapours With a Specifically Coated Optical-Fibre Sensor," Sensors and Actuators B, 11 (1993) 375-381.

Ronot et al., "Optimization and Performance of a Specifically Coated Intrinsic Optical-Fibre Sensor for the Detection of Alkane Compounds," Sensors and Actuators A, 41-42 (1994) 529-534.

Ronot-Trioli et al., "Solubility Interactions between Organic Vapors and Specific Polymeric Claddings for Optical Fiber Sensor," Sensors and Materials, vol. 7, No. 6, (1995) 383-393.

Schierbaum, "Application of Organic Supramolecular and Polymeric Compounds for Chemical Sensors," Sensors and Actuators B, 18-19 (1994), 71-76.

Hansen, George "High aspect ratio sub-micron and nano-scale metal filaments," Society for the Advancement of Material and Process Engineering, vol. 41, No. 2, pp. 2-11, (Mar. 2005).

Lonergan, Mark C. et al., "Array-Based Vapor Sensing Using Chemically Sensitive, Carbon Black-Polymer Resistors," Chem. Mater., vol. 8, No. 9, pp. 2298-2312, (1996).

Sau, K.P. et al., "Electrical conductivity of carbon black and carbon fibre filled silicone rubber composites," Die Angewandte Makromolekulare Chemie, vol. 258, No. 1, pp. 11-17, (1998).

* cited by examiner

METHODS OF MINIMIZING TEMPERATURE CROSS-SENSITIVITY IN VAPOR SENSORS AND COMPOSITIONS THEREFOR

FIELD OF THE INVENTION

The present invention relates to sensor films, and more particularly to sensor films that detect vapor analytes.

BACKGROUND OF THE INVENTION

Detection of specific target analytes, or chemical compounds, is important for many applications, including for example, detecting whether the concentration of analytes exceeds flammability limits. Target analytes are detected by sensors operating according to different detection mechanisms, known in the art. Most sensors employ a sensing component that is physically modified in the presence of specific analytes present in the environment. Thus, a sensor typically comprises a probe that includes both the sensing component and a probe body housing (including terminals for transmitting an output). The terminals are typically coupled to a processor, also part of the sensor, which analyzes the outputs received from the sensor probe to a user interface. Such a user interface typically contains an indicating device which signals a user when concentration values of an analyte have been exceeded.

Many sensors employ a sensing component that is a sensor film. Many sensor films swell, increasing in volume, while in the presence of the analytes. Various sensors available in the art utilize the physical changes in the sensor film to determine concentration of analyte present. Such sensors may include optical sensors, such as fiber optic sensors, where a beam of light is projected through an optical fiber at a sensor film cladding, and physical changes (e.g., refractive index or color) in the film are monitored. Such changes in refractive index occur when analytes are absorbed and change the physical properties of the cladding (including volumetric changes). Other sensors include surface acoustic wave sensors (SAWS), which project ultrasonic waves through the sensor film between transducers, and likewise detect any modifications in the properties of the sensor film (primarily the mass), translating those changes to the concentration of analyte present.

Another type of sensor film is a conductometric sensor, more particularly, a polymer-absorption chemiresistor sensor. A polymer-absorption chemiresistor has a polymer film sensor exposed to a surrounding atmosphere containing target analytes (chemical compounds). An electrical charge is applied across the polymer film. The polymer absorbs target analytes and this results in a volumetric change of the film, and hence the change in electrical resistance of the film.

Further, conductive particles may be distributed throughout the polymer film to enhance the sensitivity to resistance changes in the material when the volume of the polymer changes. However, any sensor film that relies upon physical changes resulting from absorption of the chemical analytes (i.e., volume, mass, refractive index, and resistance) is generally also sensitive to volumetric and resistive changes dependent on temperature. Thus, it is desirable to reduce the sensitivity to temperature and even more desirable to concurrently enhance the sensitivity to target chemical analytes. There is a need for increasing stability of a sensor film matrix by reducing or eliminating resistance fluctuations due to temperature, while maintaining and/or enhancing detection of desired chemical analytes.

SUMMARY OF THE INVENTION

In one aspect, various embodiments of the present invention provide a method for making a conductometric sensor having a reduced cross-sensitivity to temperature, where the method comprises combining materials for a sensor matrix. The materials comprise a polymer resin, a first species comprising a first conductive particle, and a second species. At least one of the polymer resin and the first species has one of a positive or a negative first temperature coefficient of resistance associated therewith. The second species has a second temperature coefficient of resistance. The second temperature coefficient of resistance is opposite to that of the first temperature coefficient of resistance. The method comprises creating a sensor matrix comprising the polymer resin, the first species and the second species. The sensor exhibits a change in resistance when exposed to one or more target analytes. In accordance with various embodiments of the present invention, the matrix exhibits a reduced change in resistance when exposed to variations in temperature.

In other aspects, certain embodiments of the present invention provide a method for improving the responsiveness of a sensor that exhibits a change in resistance when in the presence of one or more target analytes, where the method comprises creating a sensor matrix comprising a crosslinked polymer resin comprising a siloxane monomer, a first species of conductive particles comprising carbon and having a first temperature coefficient of resistance, and a second species of conductive particles having a second temperature coefficient of resistance. The first temperature coefficient of resistance influences a resistance response of the sensor matrix when exposed to variations in temperature and the second temperature coefficient of resistance has an opposite influence on the resistance response of the sensor matrix, thereby minimizing changes in the resistance of the sensor matrix upon exposure to variations in temperature.

In certain embodiments, the present invention provides a sensor composition having a reduced temperature cross-sensitivity. The composition comprises a sensor matrix comprising a crosslinked siloxane polymer resin and a plurality of conductive particles, the plurality of conductive particles comprising a first species including a conductive carbon black having an $N_2$ adsorption of between about 8 to about 25 $m^2/g$ and a DBP of about 1 to about 180 ml/100 g that has a positive temperature coefficient of resistance and a second species having a negative temperature coefficient of resistance, thereby minimizing changes in the resistance of the sensor matrix upon exposure to variations in temperature.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
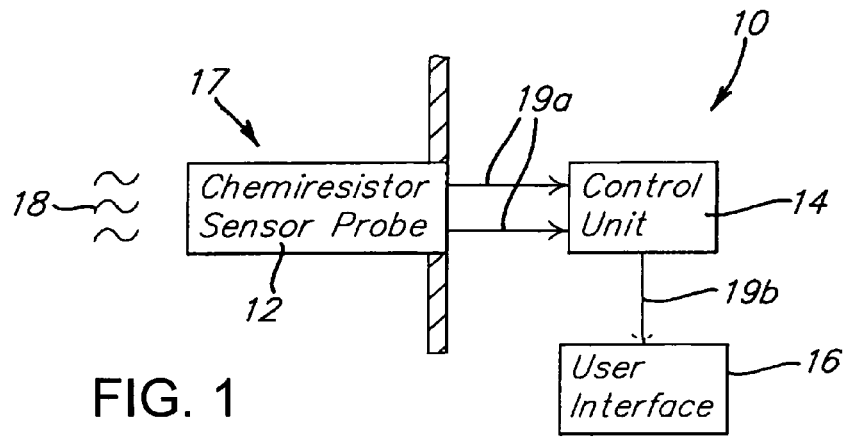
FIG. 1 is a schematic illustration of operational principles of an exemplary chemiresistor sensor.

The following description of the preferred embodiments is merely exemplary in nature and is in no way intended to limit the invention, its application, or uses.

The present invention contemplates methods of making conductometric sensors having reduced cross-sensitivity to temperature which have improved temperature stability while maintaining good sensitivity to one or more target analytes. Many materials that exhibit good electrical conductivity have resistive properties that are dependent on temperature. Electrically conductive materials that have a resistance that varies as a function of temperature are often referred to as "thermistors". As recognized by one of skill in the art, if the relationship between resistance and temperature is approximated to be linear, $\Delta R = \alpha \Delta T$, where $\Delta R$ is change in resistance, $\Delta T$ is change in temperature, and a is a first-order temperature coefficient of resistance constant. For any given material, $\alpha$ can be negative, positive or equal to zero. If $\alpha$ is positive, the resistance of the material increases with increasing temperature and the material is referred to as a positive temperature coefficient (PTC) material. If $\alpha$ is negative, the resistance decreases with increasing temperature and the device is referred to as called a negative temperature coefficient (NTC) material. Stated in another way, the resistance values for conductors can be expressed as $R=R_{ref}[1+\alpha(T-T_{ref})]$ where R is the conductive material's resistance at temperature T, $R_{ref}$ is the conductive material's resistance at a standard reference temperature $T_{ref}$, most often at 0° C. or 20° C., and $\alpha$ is the temperature coefficient of resistance constant.

There are various challenges associated with the development of robust sensor films that have superior sensitivity to one or more chemical analytes, while exhibiting stability to temperature fluctuations. For example, it is often difficult to stabilize and maintain a homogeneous distribution of conductive particles due to potential phase separation and migration within the matrix. Preferably sensors are robust and capable of withstanding mechanical shock, vibration, and thermal shock, which includes maintaining a substantially homogeneous distribution of the plurality of conductive particles for long durations of use. Further, certain otherwise desirable conductive particle species may be difficult to process and/or distribute within the matrix. Thus, design of sensor matrices accounts for these various considerations, particularly when selecting conductive particles.

Additionally, is also desirable to negate or minimize the propensity of the sensor matrix materials to vary as a function of temperature. It has been observed that some materials that perform well in a conductometric sensor matrix potentially suffer from cross-sensitivity to temperature, which potentially decreases the accuracy and effectiveness of the sensor. While it is desirable to include materials (e.g., conductive particles and/or resins) that experience minimal resistance changes as a function of temperature, often materials that exhibit a quantifiable temperature coefficient of resistance are desirable for use within a sensor matrix for various other performance reasons. In accordance with the principles of various embodiments of the present invention, a method for making a conductometric sensor having reduced cross-sensitivity to temperature includes creating a sensor matrix comprising the polymer resin and a first species comprising a first conductive particle. The first temperature coefficient of resistance is associated with at least one of the polymer resin and the first conductive particle. In some embodiments, the first temperature coefficient of resistance is associated with both the polymer resin and the first conductive particle, and the first temperature coefficient of resistance is a cumulative value, where applicable.

Thus, in accordance with various embodiments of the present invention, a sensor matrix is formed to include the materials associated with a first temperature coefficient of resistance and further includes a second species that has a second temperature coefficient of resistance that is opposite in sign to the first coefficient of resistance. In certain embodiments, the second species is a second conductive particle (or mixture of particles). In this regard, the resistance changes attributed to the first temperature coefficient of resistance materials are minimized or negated by the inclusion of materials that have a second temperature coefficient of resistance that counteracts the resistance changes associated with the materials having the first temperature coefficient of resistance, as will be described in greater detail below.

By way of background, FIG. 1 generally depicts the major components and operational principles of an exemplary chemiresistor sensor at 10. The sensor 10 is generally comprised of a chemiresistor sensor probe 12, a control unit 14, and a user interface 16. The sensor probe 12 interacts with an external environment 17 to detect the presence of analytes, or target chemical compositions 18. The sensor probe 12 generates a raw output signal 19a based on continuous detection of analytes 18 in the external environment 17. The raw output signal 19a is processed by the control unit 14. The control unit 14 transmits a calculated output signal 19b to the user interface 16 to relay analysis of the raw output signal 19a from the sensor probe 12. The user interface 16 provides information to an external user about the sensor 10 and may range from a simple alarm signal to a complex computerized screen.

Figure 2:
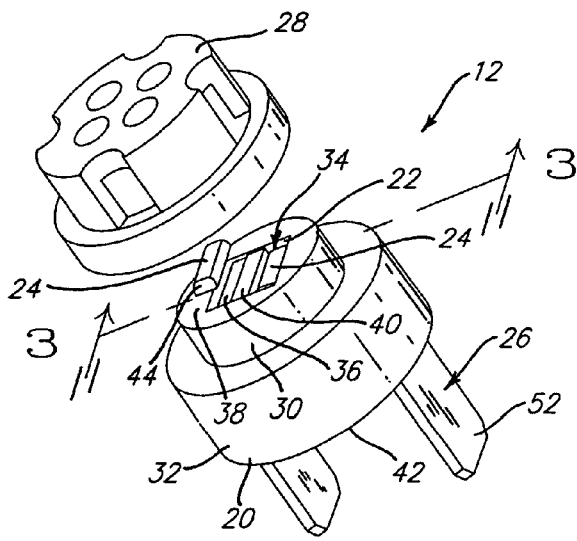
FIG. 2 is a schematic illustration of an exemplary chemiresistor sensor that can be used in accordance with the present invention.

Referring generally to FIG. 2, an example of a polymer-absorption chemiresistor sensor probe 12 compatible with the sensor film compositions of the teachings of the present invention is shown. The sensor probe 12 generally comprises a sensor housing 20, a conductive sensor film 22 covering a portion of the sensor housing 20 (FIGS. 2 and 3), a pair of electrodes 24 optionally disposed beneath and attached to the sensor terminals 26, and a protective cap 28. In lieu of electrodes, an alternate sensor embodiment is feasible, where the terminals 26 protrude into the sensor film 22, and serve a similar function to the electrodes 24 (i.e., deliver current through the sensor film 22).

The sensor housing 20 includes a first diameter portion 30 and a second diameter portion 32, wherein the first diameter portion is smaller in diameter than the second diameter portion. The first diameter portion 30 includes a sensing region 34. The sensing region 34 is comprised of two apertures 36 located within a first control surface 38 of the sensing region 34. Between the apertures 36 is a recessed second control surface 40 that extends across the sensing region 34. The second control surface 40 is slightly recessed below the first control surface 38.

Figure 3:
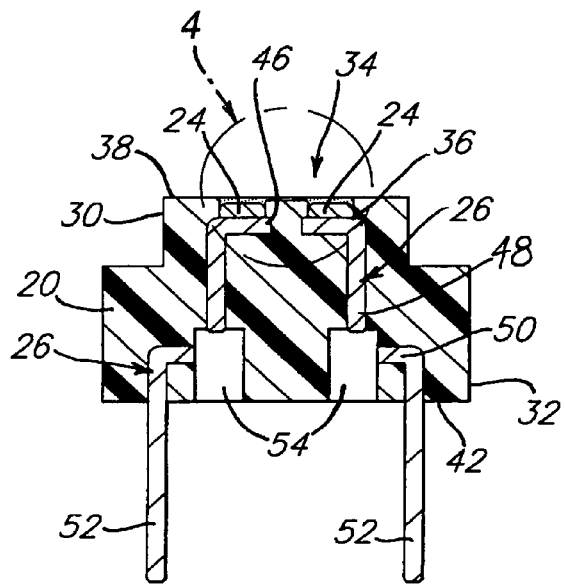
FIG. 3 is a cross-sectional view taken along line 3-3 of FIG. 2.

As best shown in FIG. 3, a cross-sectional view along line 3-3 of FIG. 2, each electrode 24 sits above the apertures 36. Terminals 26 are attached to the electrodes 24 and extend through both the first diameter portion 30 and the second diameter portion 32. The terminals 26 protrude from the housing 20 at an underside 42 of the second diameter portion 32. The electrodes 24 and terminals 26 are made of a conductive material, preferably a metal. With specific reference to FIG. 4, the electrodes 24 each comprise a horizontal porous plate or mesh that is parallel to the first control surface 38 and approximately equals the width of the aperture 36. Each electrode 24 is connected to establish a conductive pathway to terminal 26. With renewed reference to FIGS. 2 and 3, a first horizontal portion 46 of the terminal 26 makes either direct or indirect contact with the portion of the sensor film 22 seated within the apertures 36 to detect changes in the resistance of the sensor film 22. Extending from the first horizontal portion 46 is a first vertical portion 48. The first vertical portion 48 extends through the first diameter portion 30 and into the second diameter portion 32 where the first vertical portion 48 transitions to an inner terminal dogleg 50 that ends in the external terminals 52 (i.e., end leads).

At the transition point between the first vertical portion 48 to the inner terminal dogleg 50, the terminals 26 each have an aperture 54. The aperture 54 receives an alignment rod (not shown) during manufacturing to permit more precise alignment of the electrodes 24 within the housing 20. The inner terminal dogleg 50 extends to the external terminals 52 which extend from the underside 42 of the second diameter portion 32. The external terminals 52 extend from the housing 20 to a suitable length to permit interconnecting the leads to a corresponding outlet (not shown) of a suitable alert device, such as an alarm.

Figure 4:
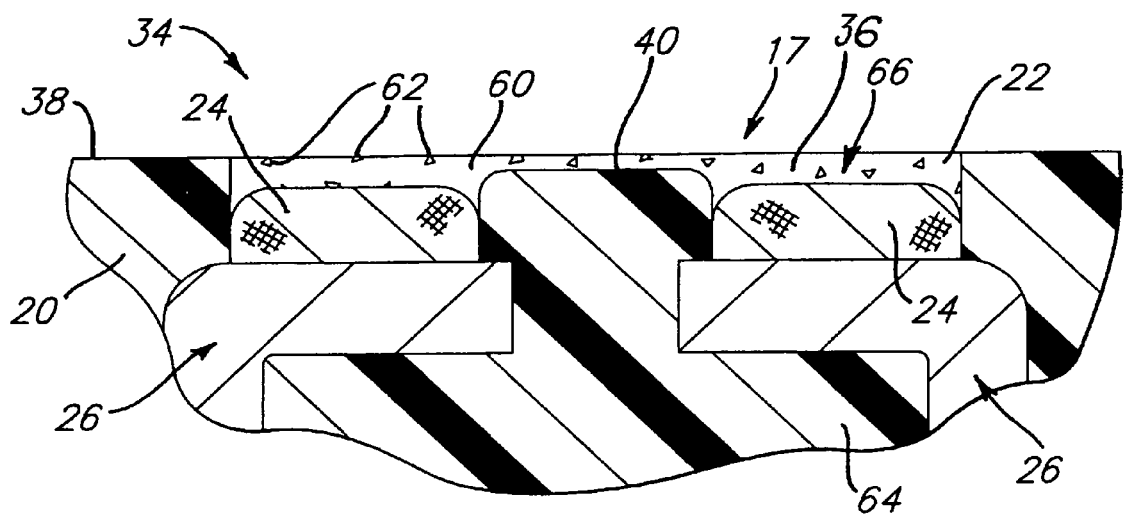
FIG. 4 is a detailed view of an exemplary sensor film region.

As best seen in FIG. 4, a detailed view of the sensing region 34 from FIGS. 2 and 3, the sensor film 22 comprises a polymer 60 with a plurality of conductive particles 62 dispersed throughout. The terminals 26 extend through a body 64 of the sensor probe housing 20 and are electrically connected to the electrodes 24. The electrodes 24 protrude into the sensing region 34 and into the sensor film 22. The electrodes 24 preferably are situated near the surface, and further across the sensor film, for even current distribution. A preferable configuration of the sensor film 22 includes conductive particles 62 distributed homogeneously throughout the sensor film 22 body forming a conductive polymeric matrix 66. By "homogeneous" it is meant that the particles are substantially evenly distributed throughout the matrix, such that any potential detrimental effects resulting from uneven and/or localized charge distribution are minimized. "Matrix" refers generally to a polymer system having conductive filler particles distributed throughout within a polymer resin.

The conductive sensor film matrix 66 is seated upon the first control surface 38 such that the matrix 66 fills the apertures 36 and spans the center second control surface 40. The matrix 66 fills the apertures 36 so that the matrix 66 is in either direct or indirect electrical contact with both of the electrodes 24. Upon exposure of the matrix 66 to target analytes, the matrix 66 volume increases by swelling.

The polymer resin 60 of the sensor film 22 can be any polymer that readily absorbs a target analyte or chemical compound, through a gas-solid interface occurring between a surface of the sensor film 22 and the surrounding gas in the external environment 17 (FIG. 1) at a rate that is relatively proportional to the concentration of the analyte in the surrounding gas. Thus, a correlation can be made between the quantity of analyte absorbed, and the concentration of the analyte in the surrounding gas. In the exemplary sensor probe 12 depicted, the change in the volume of the sensor film 22 is correlated to the concentration of the analyte present in the gas and is further related to the resistance of the sensor film 22. Of particular interest are sensor films 22 that detect vaporous hydrocarbon compound analytes, such as one or more volatile organic compounds (VOCs). Compatible polymers for detecting VOCs include siloxane polymers. A variety of siloxane based polymers are contemplated in the present invention, and further discussed below.

Figure 5:
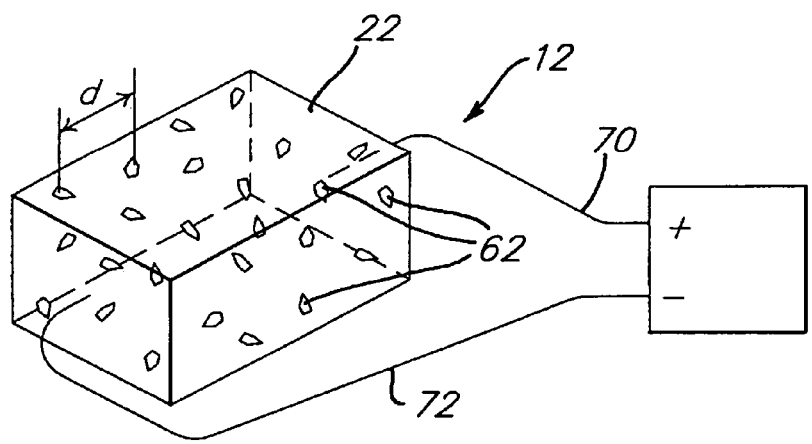
FIG. 5 is a schematic illustration of operating principles of a matrix polymer film of a polymer absorption chemiresistor.

As shown in FIG. 5, the operational principle of a polymer-absorption chemiresistor sensor probe 12 involves applying a current through the sensor film 22 between a positive 70 and a negative lead 72. Preferably, the positive and negative leads 70, 72 are terminals and/or electrodes, such as those shown at 24 and 26 in FIGS. 2-4. Conductive particles 62 are distributed throughout the sensor film 22 to enhance the electrical conductivity. Resistance measurements are taken across the sensor film 22 via monitoring of the current and potential difference across the sensor film 22 between the negative and positive leads 70, 72, and typically is measured by the processing or control unit 14 (FIG. 1) attached to the sensor probe 12. Resistance values vary with the distance "d" between the conductive particles. As this distance "d" between the conductive particles 62 increases, the resistance has a proportional relationship and thus increases. If the distance "d" decreases, the resistance also decreases. Thus, any increase or decrease in the volume of the sensor film 22 affects the overall resistance measurements.

Upon detection of a change in resistance between the positive and negative leads 70,72, the user interface 16 (FIG. 1) provides a signal indicating the presence of the substance for which the sensor film 22 has an affinity. Consequently, the change in resistance of the sensor film 22 detected by the electrodes 70, 72 indicates the presence of the target analyte. The sensor film 22 volume may increase both by changes in temperature, as well as absorption of chemical compounds, or target analytes, into the polymer of the sensor film 22. One aspect of the present invention relates to minimizing effects of volume changes of the sensor film 22 due to temperature, and maximizing the absorption and sensor film 22 sensitivity to chemical compounds. Further, as appreciated by one of skill in the art, it is desirable to have a substantially homogenous distribution of the plurality of conductive particles 62 within the sensor film 22 to negate any potential localized variations that might occur.

Further, the long-term stability and maintenance of particle distribution is important to the accuracy of the device for long-term use, because potential phase separation and migration of the particles through the matrix can cause spatial variations of the conductive particles across the sensor film that can impact the capability of the sensor film to accurately measure the presence of the target analyte compounds.

Thus, in various embodiments, the present invention provides a method for forming a conductometric sensor having a reduced cross-sensitivity to temperature. The method comprises creating a sensor matrix comprising a polymer resin and a first species comprising a first conductive particle, where at least one of the polymer resin and the first species is associated with a first temperature coefficient of resistance. The matrix further comprises a second species, which can be in certain embodiments, a conductive particle, that has a second temperature coefficient of resistance. The first temperature coefficient of resistance is opposite from the second temperature coefficient of resistance and the sensor matrix exhibits a reduced response in resistance to temperature changes or variations. It should be noted that the polymer resin and/or one or more species of conductive particles may be associated with and contribute to the overall first temperature coefficient of resistance value, and the second species is added to counteract and minimize the cumulative effects of these components. The second species may be any material that has a desirable temperature coefficient and in certain embodiments is preferably a conductive particle. Thus, the second species having the second temperature coefficient of resistance has an opposite influence on the sensor matrix's operation than that of the polymer resin and/or first species associated with the first temperature coefficient of resistance, thus minimizing changes in the sensor matrix's resistance that are attributable to variations in temperature.

Figure 6:
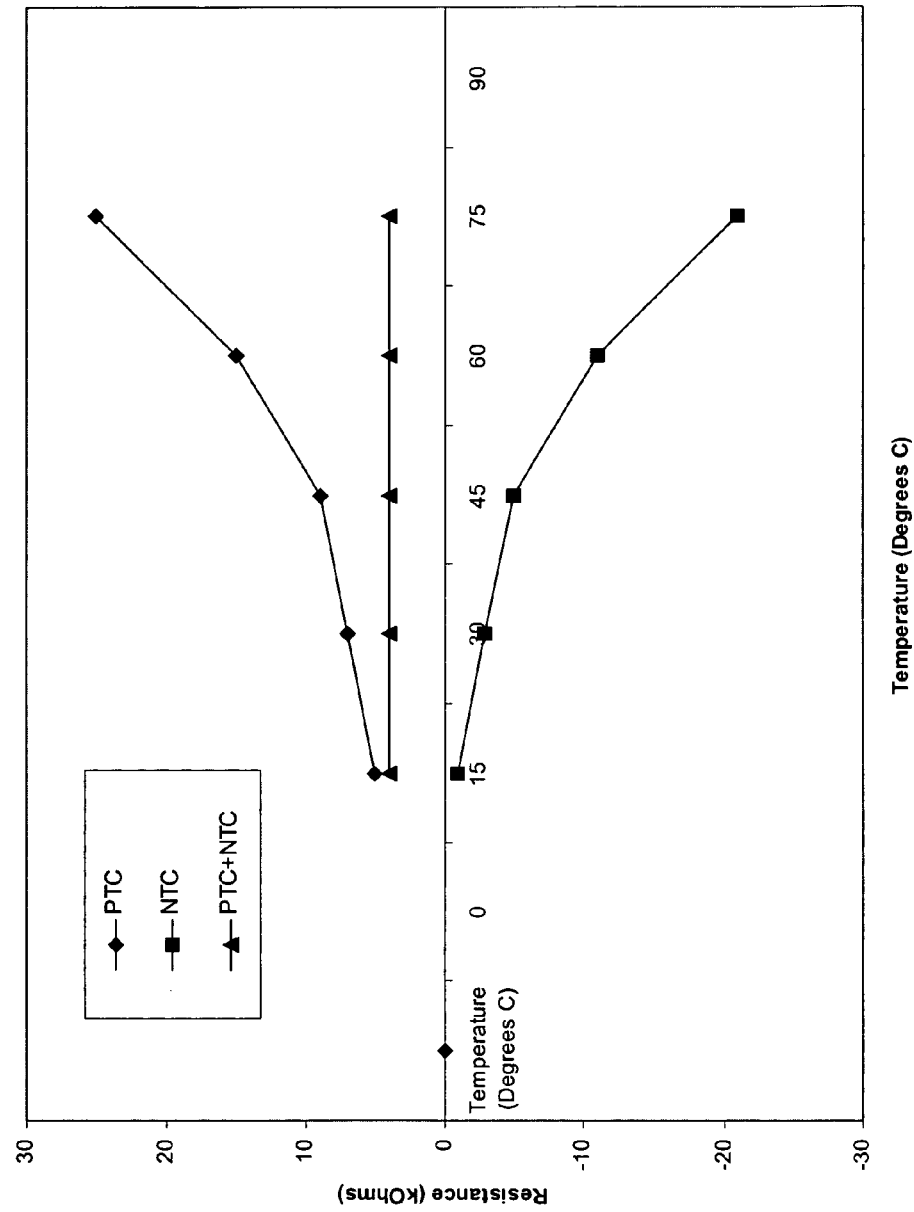
FIG. 6 is a chart showing an exemplary temperature versus resistance chart demonstrating certain aspects of the various embodiments of the present invention.

FIG. 6 demonstrates an exemplary principle of operation of certain embodiments of the present invention. The first species used in the sensor matrix is associated with a first temperature coefficient of resistance and is selected to be a conductive particle that has a positive temperature coefficient of resistance (PTC). As can be observed, as temperature increases, the resistance measurements likewise increase. A second species is added to the sensor matrix that has an opposite temperature coefficient to the first species. In the embodiment shown, the second species desirably has negative temperature coefficient of resistance (NTC). Thus, the second species exhibits a decreasing resistance when temperature increases.

In the present embodiment, a plurality of the first and the second species are conductive particles that are included in the sensor matrix. A total amount of components that are in the matrix and are further associated with the first temperature coefficient of resistance, e.g., polymer resin, the first conductive particle, or both, are provided at a desired concentration in the sensor matrix. Thus, a ratio of the total amount of components associated with the first temperature coefficient of resistance to the second species associated with the second temperature coefficient of resistance relate to an overall temperature coefficient of resistance for the sensor matrix, including all of the components contained therein. More generally, an overall temperature coefficient of resistance for the sensor matrix relates to a ratio of the first temperature coefficient of resistance to the second temperature coefficient of resistance. Thus, the components associated with the first and second temperature coefficient of resistance are preferably included at a ratio such that the resistance of the sensor matrix is substantially constant as temperature increases (or changes). In other words, an overall temperature coefficient of resistance for the sensor matrix, including all components, is optimized to approach zero and to negate temperature effects, thus a predominant resistance response of the sensor matrix is correlated to the presence or absence of target analytes. In this manner, the cross-sensitivity to temperature can be minimized, reduced, or eliminated entirely from the sensor matrix. Sensors with minimized response in resistance to temperature fluctuations have greater accuracy.

As appreciated by one of skill in the art, some materials may have a greater temperature coefficient of resistance than other materials, and may be added at lower concentrations to achieve the desired stabilization effect. Further, in some embodiments, as described above, the resistance of the crosslinked polymer resin may have resistance that is dependent upon temperature. Thus, the second species may be selected to counteract the change in resistance of both the resin and/or the first species comprising a first conductive particle in the sensor matrix, both of which can contribute to the first temperature coefficient of resistance. The ratio of the species associated with the first temperature coefficient to the species associated with the second temperature coefficient is thus dependent upon the respective values of the temperature coefficient of resistance for each species, as well as the inherent temperature coefficient of resistance for the resin material. Hence, the amounts included of each species in the matrix can be selected to achieve a desired level of resistance change over temperature changes. In the design of a conductometric sensor, there is often tolerance of a certain level of fluctuation of resistance with respect to temperature, and can vary for individual applications, depending on the overall resistance values exhibited in response to the presence of one or more target analytes. Further, the amount of the species respectively having the first and second temperature coefficients of resistance includes other factors in the sensor matrix composition design, including sensitivity to analytes, ease of processing of the polymer matrix during fabrication, and the resistance of the sensor.

For example, certain sensors are "low-resistance" applications, where the overall change in resistance tends to be relatively low (generally less than about 1 kOhm), and thus, sensitivity to changes in resistance due to temperature fluctuations may impact accuracy far more than those where the resistance changes are significant. In certain embodiments of the present invention, it is preferred that the fluctuations in resistance of a sensor matrix due to temperature (through a range of operating temperatures of the sensor) is less than about 25%, more preferably less than about 20%, even more preferably less than about 15%, even more preferably less than about 10%, and most preferably less than about 5% of the total resistance.

Thus, in accordance with certain embodiments of the present invention, the first temperature coefficient is a positive temperature coefficient and the second temperature coefficient is a negative temperature coefficient. In other specific embodiments of the present invention, the first temperature coefficient is a negative temperature coefficient and the second temperature coefficient is a positive temperature coefficient. Further, as appreciated by one of skill in the art, the plurality of conductive particles in the sensor is not limited to two species, and can comprise multiple distinct species of conductive particles to enhance sensor operations. Thus, the plurality of conductive particles may contain multiple distinct species of conductive particles, creating various blends of conductive particles having different temperature coefficients of resistance, as appreciated by one of skill in the art. Any number of combinations of species of conductive particles is contemplated by the present invention.

One particularly efficacious conductive particle for use in a conductometric sensor matrix composition is a carbon black material. In particular, one preferred carbon black has a relatively low surface area and DBP absorption values, in essence, conductive particles that are larger in particle size and lower in aggregate size. Carbon black particles may be characterized by particle size, surface area per weight, and structure. A correlation generally exists between surface area and particle size, where a smaller particle diameter gives rise to a higher surface area. Likewise, a lower surface area value generally indicates a larger particle size diameter. Surface area is generally tested by the level of nitrogen adsorption ($N_2$) values in $m^2/g$. Testing procedures for nitrogen adsorption are outlined for example, in ASTM test D3037-91. Conductive carbon black particles for use as one species in accordance with the present invention preferably have a $N_2$ adsorption value (surface area per weight) of between about 8 to about 25 $m^2/g$. The most preferred ranges of $N_2$ adsorption for these carbon black species are between about 10 to about 15 $m^2/g$.

Conductive carbon black particles are characterized by structure, or the configuration, of individual particles forming an aggregate. Structure can be tested by oil dibutylphthalate (DBP) absorption in accordance with test procedure ASTM D2414, where DBP is added to 100 grams of carbon black while being mixed to generate a value of DBP ml/100 grams. A sharp increase in the torque determines the DBP value. This test indicates the structure of the particles by measuring the size of the particle aggregate. When one of the species of the plurality of conductive particles is selected to be carbon black, the DBP preferably ranges from about 1 to about 180 ml/100 g.

Carbon blacks can be formed by a variety of processing conditions, and the method of formation often relates to the physical parameters of the carbon black. Two main forms of carbon black are thermal black, formed by thermal decomposition, or cracking, of natural gas. Furnace blacks are formed in an incomplete combustion furnace process, which typically entails burning or oxidizing of a carbon rich oil-based feedstock at high temperatures. Furnace blacks generally have a small particle size, as where thermal blacks tend to have the largest particle sizes of carbon blacks. Fine thermal blacks typically have an average particle size in the range of about 100 to 200 nm, and fall into the class of carbon blacks designated N800 series. One particularly preferred fine thermal black is the class N880, which varies in average particle size, but is generally between about 90 to about 120 nm. Examples of commercially available conductive carbon black particles that fulfill the preferred physical characteristic ranges for one of the species of conductive particles as described above include: Asahi 15HS or AS N880, both manufactured by Asahi Carbon Co., Ltd. of Japan; or CC N880 from Cancarb Ltd. of Alberta, Canada; and SPHERON® 5000 or SPHERON® 6000 both available from the Cabot Corporation of Boston, Mass. Preferred ranges of the mean particle size are from about 90 to about 400 nanometers, preferably less than 200 nm, and most preferably less than about 150 nm. One particularly preferred large particle size carbon black is the Asahi 15HS, which has an average particle size of between about 100 to about 130 nm, an $N_2$ adsorption of about 14 $m^2/g$, a DBP of about 85 ml/100 g, and a density of about 1.8 g/cc. Generally speaking, the large particle size carbon black particles behave as positive temperature coefficient of resistance (PTC) materials.

In various embodiments, an electrically conductive metal particle can be selected as a conductive particle in the sensor matrix. Examples of such electrically conductive metals include nickel, gold, silver, manganese, copper, iron, cobalt, magnesium, aluminum, and/or mixtures and alloys thereof. Particularly preferred electrically conductive metal particles include gold, silver, and nickel. Other exemplary suitable conductive particles that can be used with the present invention, as recognized by one of skill in the art, include, for example, platinum, graphite (i.e., hexagonally crystallized carbon), carbon black particles not described above, conductive metal borides, nitrides, carbides, or mixtures thereof. These materials have both positive and negative temperature coefficients of resistance, and can be evaluated to determine their behavior in a sensor matrix.

In certain embodiments of the present invention, the conductive particle has an axial geometry, and includes fibers, wires, whiskers, filaments, tubes, and the like. Such particles having a cylindrical or rod shape with an elongated axis have an axial geometry. Generally, an aspect ratio (AR) for cylindrical shapes (e.g., a rod or fiber) is defined as AR=L/D where L is the length of the longest axis and D is the diameter of the cylinder or fiber. Exemplary axial geometry particles suitable for use in the present invention generally have high aspect ratios, ranging from about 500 to about 5,000, for example, where an average diameter of the particle ranges from less than 1 nm to about 30 nm, and the length of the nanoparticle can be from several hundred nanometers to greater than about 10 μm. Axial geometry conductive particles include carbon nanotubes, which exhibit excellent electrical conductivity, for example, 100 S/cm. In certain embodiments, the conductive particle is a carbon nanotube (either multi-walled or single-walled) or a graphene structure conductive particle.

In an embodiment where a first species of conductive particle is selected to be the large particle size, low surface area carbon black, which is a PTC material, a second species preferably has an opposite temperature coefficient of resistance, specifically it is an NTC material. The second species can be selected from any of the materials described above that are NTC materials. Other suitable NTC materials for conductive particles for use in the sensor matrix of the present invention comprise metal oxides of magnesium, aluminum, manganese, nickel, cobalt, copper, iron, and mixtures thereof, for example. Thus, such NTC materials include, for example, $MgO$, $Al_2O_3$, $NiO$, $Mn_3O_4$, $Co_3O_4$, $Cu_2O_3$, $Fe_2O_3$, and $Ni_{(1-x)}Mn_{(2-x)}O_4$, where x ranges from greater than 0 to less than about 1. One example of a suitable NTC material is an ultra-high purity nickel oxide with greater than 78% nickel, which is commercially available as "Green Nickel Oxide" from Novamet Specialties Product Corp. of Wyckoff, N.J.

As described above, the total amount of the plurality of conductive particles comprising the first and second species is dependent on the individual characteristics of the particle selected, in particular, the respective temperature coefficients of resistance, but can be present in the matrix from about 25 to about 75 percent by weight of the total mixture. In certain embodiments, the conductive particles are present at about 5 to about 50 parts per hundred resin (phr).

Distribution of the conductive particles 62 throughout the polymer base 60 can be achieved by mixing the first and second species of conductive particles 62 with a polymer resin prior to application on the sensor probe 12 to form a matrix mixture which forms the polymer base 60 of the sensor film 22. In other embodiments, the first and second species of conductive particles are pre-mixed. The conductive particles mixture 62 is then mixed with a polymer resin prior to application on the sensor probe 12 to form a matrix mixture which forms the polymer base 60 of the sensor film 22. Preferably, the conductive particles 62 are homogeneously distributed throughout the polymer matrix base 60 to enhance the uniformity of resistance measurements, as discussed above. The use of the conductive particles 62 in chemiresistor sensor films 22, significantly reduces and/or minimizes the cross-sensitivity of the sensor film 22 to temperature and enhances accuracy of the detection of chemical analytes over the prior art use of conductive particles. Thus, there is a significant decrease in temperature cross-sensitivity.

In various embodiments of the present invention, the sensor film 22 comprises a polymer resin. In various embodiments, the polymer resin comprises siloxane. A "siloxane polymer" as used herein, refers to a cross-linked polymer that has a basic backbone of silicon and oxygen with side constituent groups that may be the same or different, generally described by the structural repeating unit $(-O-SiRR'-)_n$, where R and R' may be the same or different side constituent groups, and n may be any value above 2 designating the repetition of the SRU in the polymer backbone. Thus, such siloxane polymers generally comprise at least one siloxane monomer or SRU. Siloxane polymers are also known in the art as "silicone" polymers. Siloxane polymers may include polyheterosiloxanes, where side groups and/or structural repeating units may be different entities (having different side constituent groups), such as, for example, the siloxane co-polymer described by the nominal SRU formula, $(-O-SiRR')_n-(-O-Si-R''R''')_m$, wherein R and R' are distinct side groups from R" and R'''. Further R and R' may be different from one another, likewise the same may be true for R"

and R'''. Such siloxane polymers may terminate in any variety of terminal groups, such as for example, trimethyl silyl ((CH$_3$)$_3$Si) terminated siloxane, or ethyl vinyl terminated siloxane.

In one embodiment of the present invention, the polymer of the sensor film is a cross-linked dimethylsiloxane (—O—SiRR')$_n$, where R and R' are both CH$_3$. Such side groups may be referred to as "branched" indicating side groups attached to the siloxane backbone.

In an embodiment of the present invention, the sensor film 22 comprises a crosslinked siloxane polymer base, wherein the siloxane polymer backbone has at least one monomer with a large hydrocarbon substituted side group represented by R' in the nominal general formula for the structural repeating unit (—O—SiRR')$_n$. A "hydrocarbon side group", as used herein, includes any hydrocarbon or hydrocarbon derived side group with two carbon atoms or greater. Examples of such hydrocarbon side groups include: alkyl and aryl groups greater than an ethyl group, branched alkyl groups, aromatics, modified hydrocarbon compounds comprising a polar group, or mixtures thereof. Polar group modified hydrocarbons incorporate a polar molecule or molecular group into the hydrocarbon side group structure, with the effect of imparting polarity on the entire side group. Such polar atoms or groups may include, for example, oxygen, nitrogen, or ammonia, cyano or hydroxyl groups. Examples of preferred hydrocarbon side groups include without limitation: ethyl, propyl, butyl, pentyl, hexyl, heptyl, octyl, nonyl, decyl, phenyl, alkylphenyl, cyclopentyl, and phenylpropyl. Particularly preferred hydrocarbon side groups are alkyl groups with eight or more carbon atoms (octyl groups or higher). Other preferred hydrocarbon side groups comprising a polar group include, for example, butylated aryloxypropyl, N-pyrrolidonepropyl, cyanopropyl, benzyltrimethyl ammonium chloride and hydroxyalkyl.

One example of such a siloxane having a large hydrocarbon side group includes an octyl hydrocarbon side group that forms an octylmethylsiloxane monomer. It is preferable that the siloxane polymer according to the present embodiment is crosslinked, and thus also contains a functional group capable of crosslinking during any subsequent curing or crosslinking processes. Preferred crosslinked siloxane polymers include those polymers (including homopolymers and copolymers) having at least one large hydrocarbon side substituent group. As used herein, the term "polymer" encompasses homopolymers and copolymers. The term "copolymer" generically refers to a polymeric structure that has two or more monomers polymerized with one another, and includes polymers such as terpolymers with three combined monomers. A "homopolymer" refers to a polymer comprised of a single monomer. One example of a preferred crosslinked siloxane having a copolymer (e.g., terpolymer) structure is poly(vinylmethylsiloxane-octylmethylsiloxane-dimethylsiloxane). Thus, the terpolymer structure has vinyl functional groups that are capable of crosslinking when exposed to crosslinking or curing agents. Ranges of the quantity of monomers in the terpolymer include (3-5% vinylmethylsiloxane)-(35-75% octylmethysiloxane)-(20-62% dimethylsiloxane), wherein the octyl is the hydrocarbon side group R', incorporated into the siloxane monomer, and R is a methyl side group. Another example of a preferred crosslinked siloxane having a large hydrocarbon side group according to the present invention is a polyphenylmethylsiloxane, where the phenyl is the large hydrocarbon side group and the polymer has vinyl terminal groups for subsequent crosslinking.

In certain embodiments, the terpolymer having a large hydrocarbon side group is further reacted with another polymer. Preferably, this additional polymer likewise comprises siloxane, and may be a homopolymer or copolymer, as described above, with functional groups capable of crosslinking. Such a polymer is sometimes referred to as a "crosslinking" agent. Thus, in a certain embodiment of the present invention, the additional copolymer comprises a polydimethyl siloxane. In another embodiment, the additional copolymer comprises a siloxane copolymer further comprising an additional large hydrocarbon side group. For example, one suitable polymer comprises (7-13% hydroxymethylsiloxane)-(87-93% octylmethylsiloxane), has an average molecular weight of about 6000, is capable of cross-linking with the first copolymer described above and is commercially available from Gelest, Inc. of Tullytown, Pa. as the product HAM-301. Another example of a suitable polymer that functions as a hydrosilylation crosslinking reagent, such as polyethylhydrosiloxane, which is commercially available as the product HES-992, also from Gelest, Inc.

Incorporation of large hydrocarbon side groups into monomers (which are further incorporated into polymers according to the present invention) is achieved by polymerization performed in a conventional manner. Such a monomer, having a side group, is preferably functionalized by incorporating a reactive functional group (e.g., epoxy, amine, mercapto, methacrylate/acrylate, acetoxy, chlorine; hydride or vinyl; or hydroxyl groups) to facilitate incorporation into the siloxane backbone by polymerization, such as by conventional methods known in the art. In the case of poly(vinylmethylsiloxane-octylmethylsiloxane-dimethylsiloxane), discussed above, the octylmethylsiloxane monomer is incorporated into a copolymer with other monomers of dimethylsiloxane and vinylmethyl siloxane, where the octylmethylsiloxane monomer is preferably present in the range of from about 35% to about 75%. The octylmethylsiloxane monomer displaces the dimethylsiloxane monomer. In the case of polyphenylmethylsiloxane, substantially all of the polymer chain comprises the phenylmethylsiloxane monomer, except for the terminal ends of the siloxane polymer which are vinyl terminated (e.g., dimethylvinyl terminated siloxane). Such monomer ranges are exemplary and non-limiting and are dependent upon specific characteristics of the individual monomers employed. It is preferable to maximize the quantity of large hydrocarbon side group substituted monomers in the siloxane polymer.

After the large hydrocarbon side group siloxane base copolymer (or plurality of distinct copolymers) is formed (by a conventional polymerization reaction), the polymer(s) further undergo crosslinking after incorporation into the sensor film. Such crosslinking may be carried out by conventional means, such as by exposure to irradiation or peroxide, moisture cure by a condensation reaction, or a hydrosilylation reaction in the presence of a catalyst. Any method of crosslinking siloxane polymers may be used with the present invention, as recognized by one of skill in the art. A preferred method of crosslinking is the hydrosilylation reaction in the presence of a catalyst, which can generally be conducted at lower temperatures and where the control over the degree of crosslinking is greater.

Crosslinking by hydrosilylation generally requires a catalyst and a crosslinking (curing) reagent which reacts with accessible functional groups on at least some of the side groups within the siloxane polymer. One example of a hydrosilylation crosslinking reaction includes, for example, polyethylhydrosiloxane, discussed above, as a crosslinking reagent in the presence of a platinum catalyst to result in a crosslinked siloxane polymer. The hydrosilylation reaction facilitates crosslinking between neighboring siloxane chains at the functional group sites. Other feasible catalyst systems that may be used for hydrosilylation (in addition to platinum) in the present invention include, for example: platinum carbonyl cyclovinylmethyliloxane complex used for elevated cures, such as SIP 6829 which is also commercially available from Gelest, Inc.; Rh(I) catalysts such as $(PPh_3)_3RhCl$ or $[(C_2H_4)_2RhCl]_2$, Ni catalysts, $(PPh_3)PdCl_2$, $Rh_2(OAc)_4$, $Ru_3(CO)_{12}$, and $Co_2(CO)_8$ and equivalents thereof. Functional groups must be present along the siloxane backbone or at the chain ends to allow for subsequent crosslinking after polymerization. The distinct monomers within any of the copolymers may be distributed randomly or may be regularly ordered.

The crosslinking reaction is preferably achieved through a hydrosilylation reaction by adding an appropriate curing reagent and a catalyst. The rate of reaction for crosslinking is dependent on temperature and is accelerated when temperature is raised, a catalyst is added, or both. Temperature may be used to control the rate of reaction to coincide with processing needs. Further, the addition of the catalyst may be prolonged until the mixture is ready to be processed for application onto the sensor. Preferably, the curing reagent is added in the range of about 1 to about 5 weight % of the total polymer and curing reagent to form a polymer mixture. Preferably, catalyst is charged to the polymer mixture from about 0.05 to 1 weight percent of the total polymer mixture (excluding conductive particles).

A matrix mixture may be formed by admixing the plurality of conductive particles (where the first and second species are pre-mixed together to form a conductive particle mixture) into the polymer resin (prior to charging with the catalyst). The plurality of conductive particles are added in a range of from about 25 to about 75% of the total mixture depending on particle characteristics, including tendency to disperse in the matrix, inter alia. It is preferred that the plurality of conductive particles is well mixed into the polymer mixture for even distribution. The polymer or matrix mixture can be blended or mixed by equipment known in the art, such as for example, a mixer (e.g., a BANBURY® or BRABENDER® mixer), a kneader, a monoaxial or biaxial extruder (e.g., single-screw or twin-screw extruders).

The handling and flowability of a matrix mixture is dependent on the rate of crosslinking once the catalyst is added, which affects the viscosity of the mixture. The amount of time that remains for handling is generally known as the "pot life", and may range from many hours at room temperature to less than an hour if temperatures are raised to above room temperature. The crosslinking or curing reaction may be prolonged by addition of inhibitors, which are well known in the art, as a means for retarding the reaction. The crosslinking or curing reaction can be performed entirely at room temperature, or may be accelerated by heating the mixture, depending on the processing needs. Such curing temperatures range from about 30° C. to about 250° C. The mixture is then applied to the sensor surface by conventional application means (e.g., doctor blade, casting, lamination, extrusion, pad printing, spraying or silk screening). After application, further sensor components and processing may be completed, such as applying a protective cap. It is preferred that the curing occurs by placing the sensor with a matrix mixture applied into an oven at elevated temperature, for example, for 3 hours at 120° C. or for 8 hours at 130° C. However, many variations of curing the siloxane polymer in the matrix mixture are feasible with the present invention.

In one embodiment of the present invention, a method for improving sensor accuracy and the responsiveness of a sensor that exhibits a change in resistance when in the presence of one or more target chemical analytes is provided. The method comprises creating a sensor matrix comprising a crosslinked polymer resin comprising a siloxane monomer, a first species of conductive particles having a first temperature coefficient of resistance. Any of the sensor materials described previously are suitable for use in the present embodiment. The first species of conductive particles preferably comprises carbon. The sensor matrix further comprises a second species of conductive particles that has a second temperature coefficient of resistance. The first temperature coefficient of resistance influences a resistance response of the sensor matrix when exposed to variations in temperature and the second temperature coefficient of resistance has an opposite influence on the resistance response of the sensor matrix. The inclusion of the second species in the sensor matrix thereby minimizes changes in the resistance of the sensor matrix upon exposure to variations in temperature. The creating can include admixing the polymer resin with the first conductive particle and the second species comprising a second conductive particle, a curing reagent, and a catalyst to form a matrix mixture. The matrix mixture is then applied on a sensor probe and then the matrix mixture is crosslinked.

In yet another embodiment, the present invention relates to an embodiment of a sensor composition that has reduced cross-sensitivity to temperature. Any of the sensor materials described previously are suitable for use in the sensor composition. In one embodiment, the sensor composition comprises a sensor matrix comprising a crosslinked siloxane polymer resin and a plurality of conductive particles comprising a first species. The first species includes a conductive carbon black having an $N_2$ adsorption of between about 8 to about 25 $m^2/g$ and a DBP of about 1 to about 180 ml/100 g with a positive temperature coefficient of resistance. A second species has a negative temperature coefficient of resistance. The changes in the resistance of the sensor matrix are minimized when the sensor is exposed to variations in temperature. The following example further exemplifies one of various embodiments of the present invention.

EXAMPLE 1

A sensor film polymer matrix having a blend of conductive particles including a PTC large particle size conductive carbon black and a NTC ultra high purity nickel oxide is prepared by adding the following materials into a mixer: 3 grams of a 3-5% vinylmethylsiloxane-44-52% octylmethylsiloxane-44-51% dimethylsiloxane terpolymer (commercially available as VAT 4326 from Gelest, Inc.) which is a crosslinked large hydrocarbon side group substituted siloxane polymer; 8 grams of a 7-13% hydromethylsiloxane-87-93% octylmethylsiloxane copolymer available as HAM-301 from Gelest; 10 grams of Asahi 15HS (a large particle size carbon black available from Asahi Carbon Company having an $N_2$ value of 14 $m^2/g$ and a DBP of 85 ml/100 g); 10 grams of ultra high purity nickel oxide available from Novamet Specialty Chemical Corp as Green Nickel Oxide; 0.1 grams of a platinum carbonyl cyclovinylmethylsiloxane catalyst complex (commercially available as SIP 6829 from Gelest, Inc.). The materials are mixed in a BRABENDER® mixer for 15 minutes at 30° C. and 80 rpm to form a matrix mixture. The mixture is then applied in a groove over electrodes in a sensor structure by a doctor blade. The sensor structure having the matrix mixture applied is then cured for 8 hours at 130° C.

EXAMPLE 2

A sensor film polymer matrix having a blend of conductive particles including a PTC large particle size conductive carbon black and a NTC ultra high purity nickel oxide having a different polymer system from Example 1 is prepared by adding the following materials into a mixer: 96.9 parts by weight VAT-4326 a (3-5% vinylmethylsiloxane)-(35-40% octylmethylsiloxane)-(dimethylsiloxane) terpolymer available from Gelest; 3.1 parts by weight HES 992 (a polyethylhydrosiloxane curing agent from Gelest); 0.1 parts by weight SIP 6829 (a platinum carbonyl cyclovinylmethylsiloxane catalyst complex); and 50 parts per hundred resin (phr) of Asahi 15HS (a large particle size carbon black available from Asahi Carbon Company having an $N_2$ value of 14 $m^2$/g and a DBP of 85 ml/100 g); 50 phr of ultra high purity nickel oxide available from Novamet Specialty Chemical Corp as Green Nickel Oxide. The materials are mixed in a BRABENDER® mixer for 15 minutes at 30° C. and 80 rpm to form a matrix mixture. The mixture is then applied in a groove over electrodes in a sensor structure by a doctor blade. The sensor structure having the matrix mixture applied is then cured for 3 hours at 120° C.

The sensor films according to the various embodiments of the present invention provide a robust sensor having reduced sensitivity to temperature changes, thus improving the sensor film operation by enhancing accuracy of detection of analyte concentration. The trade-off between temperature sensitivity (swelling) and sensitivity to analytes has been improved, by enabling the use of materials that have superior sensitivity to one or more target analytes, while reducing and/or minimizing cross-sensitivity to temperature. The description of the invention and examples provided herein is merely exemplary in nature and, thus, variations that do not depart from the gist of the invention are intended to be within the scope of the invention. Such variations are not to be regarded as a departure from the spirit and scope of the invention.

What is claimed is:

1. A method for making a conductometric sensor having a reduced cross-sensitivity to temperature, the method comprising:
    combining materials for a sensor matrix comprising a polymer resin, comprising an octylmethylsiloxane monomer, a first species comprising a first conductive particle, and a second species, wherein at least one of said polymer resin and said first species has one of a positive or a negative first temperature coefficient of resistance associated therewith, and said second species has a second temperature coefficient of resistance, wherein said second temperature coefficient of resistance is opposite to that of said first temperature coefficient of resistance; and
    creating a sensor matrix comprising said polymer resin, said first species and said second species, wherein said polymer resin crosslinked and said sensor exhibits a change in resistance when exposed to one or more target analytes;
    whereby said matrix exhibits a reduced change in resistance when exposed to variations in temperature.

2. The method according to claim 1, wherein said second species comprises a second conductive particle having said second temperature coefficient of resistance.

3. The method according to claim 2, wherein said first conductive particle is selected from the group consisting of: nickel, gold, silver, manganese, copper, iron, cobalt, magnesium, platinum, aluminum, oxides, alloys, and mixtures thereof; graphite; carbon black; graphene; and borides, nitrides, carbides, or mixtures thereof.

4. The method according to claim 2, wherein at least one of said first and said second conductive particles comprises carbon.

5. The method according to claim 2, wherein said creating further comprises:
    admixing said polymer resin, said first species comprising said first conductive particle, said second species comprising said second conductive particle, a curing reagent, and a catalyst to form a matrix mixture;
    applying said matrix mixture to a sensor probe; and
    crosslinking said matrix mixture.

6. The method according to claim 1, wherein said first temperature coefficient of resistance is positive and said second temperature coefficient of resistance is negative.

7. The method according to claim 6, wherein said first conductive particle comprises conductive carbon black particles having an $N_2$ adsorption of between about 8 to about 25 $m^2$/g and a DBP of about 1 to about 180 ml/100 g.

8. The method according to claim 6, wherein said second species comprises a conductive particle comprising at least one oxide of magnesium, aluminum, manganese, nickel, cobalt, copper, iron, or mixtures thereof.

9. The method according to claim 1, wherein said first temperature coefficient of resistance is negative and said second temperature coefficient of resistance is positive.

10. The method according to claim 1 wherein said one or more target analytes comprise volatile organic compounds (VOCs).

11. The method according to claim 1 wherein an overall temperature coefficient of resistance for said sensor matrix relates to a ratio of said first temperature coefficient of resistance to said second coefficient of resistance.

12. The method according to claim 11 wherein said overall temperature coefficient of resistance for said sensor matrix relates to a ratio of a first amount of components within said matrix associated with said first temperature coefficient of resistance to a second amount of components associated with said second coefficient of resistance.

13. A method for improving the responsiveness of a sensor that exhibits a change in resistance when in the presence of one or more target analytes, the method comprising:
    creating a sensor matrix comprising a crosslinked polymer resin comprising an octylmethylsiloxane monomer, a first species of conductive particles comprising carbon and having a first temperature coefficient of resistance, and a second species of conductive particles having a second temperature coefficient of resistance, wherein said first temperature coefficient of resistance influences a resistance response of said sensor matrix when exposed to variations in temperature and said second temperature coefficient of resistance has an opposite influence on said resistance response of said sensor matrix, thereby minimizing changes in the resistance of said sensor matrix upon exposure to variations in temperature.

14. The method according to claim 13 wherein said first species of conductive particles comprises conductive carbon black particles having an $N_2$ adsorption of between about 8 to about 25 $m^2$/g and a DBP of about 1 to about 180 ml/100 g.

15. The method according to claim 13 wherein said second species comprises a conductive particle comprising at least one oxide of magnesium, aluminum, manganese, nickel, cobalt, copper, iron, or mixtures thereof.

16. A sensor composition having a reduced temperature cross-sensitivity, the composition comprising:
    a sensor matrix comprising a crosslinked siloxane polymer resin comprising an octylmethylsiloxane monomer and a plurality of conductive particles, said plurality of conductive particles comprising a first species including a conductive carbon black having an $N_2$ adsorption of between about 8 to about 25 $m^2/g$ and a DBP of about 1 to about 180 ml/100 g that has a positive temperature coefficient of resistance and a second species having a negative temperature coefficient of resistance, thereby minimizing changes in the resistance of said sensor matrix upon exposure to variations in temperature.

17. The sensor material according to claim 16 wherein said second species comprises a conductive particle comprising at least one oxide of magnesium, aluminum, manganese, nickel, cobalt, copper, iron, or mixtures thereof.

* * * * *

UNITED STATES PATENT AND TRADEMARK OFFICE
CERTIFICATE OF CORRECTION

PATENT NO. : 7,708,947 B2  Page 1 of 1
APPLICATION NO. : 11/265225
DATED : May 4, 2010
INVENTOR(S) : Jeffrey A. West and Praveen C. Ramamurthy It is certified that error appears in the above-identified patent and that said Letters Patent is hereby corrected as shown below:

Column 3,
Line 27, "and a" should be --and α--.

Column 15,
Line 51, Claim 1, after "resin", insert --is--.

Signed and Sealed this
Fifteenth Day of March, 2011

David J. Kappos
*Director of the United States Patent and Trademark Office*